US005776685A

United States Patent [19]

Riedel

[11] Patent Number: 5,776,685
[45] Date of Patent: Jul. 7, 1998

[54] PROTEIN KINASE C ASSAY

[75] Inventor: Heimo Riedel, Jamaica Plain, Mass.

[73] Assignee: Joslin Diabetes Center, Boston, Mass.

[21] Appl. No.: 752,047

[22] Filed: Nov. 19, 1996

Related U.S. Application Data

[63] Continuation of Ser. No. 293,744, Aug. 22, 1994, abandoned, which is a continuation of Ser. No. 89,043, Jul. 19, 1993, abandoned.

[51] Int. Cl.$^6$ .............................. C12Q 1/68; C12N 15/00; C12N 9/12; C07H 21/02
[52] U.S. Cl. ........................... 435/6; 435/172.3; 435/194; 435/254.21; 435/320.1; 536/28.1
[58] Field of Search ...................... 435/6, 172.3, 320.1, 435/194, 254.21; 536/23.2

[56] References Cited

U.S. PATENT DOCUMENTS 4,980,281  12/1990  Housey et al. .......................... 435/29

OTHER PUBLICATIONS

Goode et al. (1994), "Expression of Mammalian Protein Kinase C in Schizosaccharomyces pombe: Isotype-specific Induction of Growth Arrest, Vesicle Formation, and Endocytosis," Molecular Biology of the Cell 5: 907–920.
Ito et al. (1983), "Transformation of Intact Yeast Cells Treated with Alkali Cations." J. Bacteriol. 153: 163–168.
Kikkawa et al. (1987), "The common structure and activities of four subspecies of rat brain protein kinase C family." FEBS Lett. 223: 212–216.
Osada et al., (1988), "Rapid Screening Method for Inhibitors of Protein Kinase C." J. Antibiotics (Tokyo) 41: 925–931.
Osada et al. (1990), "A Phorbol Ester Receptor/Protein Kinase, nPKCη, a New Member of the Protein Kinase C Family Predominantly Expressed in Lung and Skin." J. Biol. Chem. 265: 22434–22440.
Burns et al. (1991), "Protein kinase C contain two phorbol ester binding domains" J. Biol. Chem. 266: 18330–18338.
Castagna et al. (1982), "Direct activation of calcium–activated, phospholipid–dependent protein kinase by tumor-–promoting phorbol esters" J. Biol. Chem. 257: 7847–7851.
Coussens et al. (1986), "Multiple, distinct forms of bovine and human protein kinase C suggest diversity in cellular signaling pathways." Science 233: 859–866.
Fields et al. (1991), "Genetic suppression analysis of the function of a protein kinase C (PKC1 gene product) in Saccharmyces cerevisiae Cell cycle progression: the SKC$^d$ Mutations." Cold Spring Harbor Symp. Quant. Biol. 56: 51–60.
Gescher et al. (1985), "Antiproliferative properties of phorbol ester tumor promoters" Pharmacology 34: 2587–2592.
House et al. (1987), "Protein kinase C contains a pseudosubstrate protope in its regulatory domain" Science 238: 1726–1728.
Houslay et al. (1991), "Crosstalk: A pivotal role for protein kinase C in modulating relationships between signal transduction pathways." Eur. J. Biochem. 195: 9–27.

Hu et al. (1990), "Modulation of the insulin–like growth factor II/mannose 6–phosphate receptor in microvascular endothelial cells by phorbol ester via protein kinase C." J. Biol. Chem. 265: 13864–13870.
Huang et al. (1990), "Role of protein kinase C in cellular regulation." BioFactors 2: 171–178.
Iwai et al. (1992), "Catalytic properties of yeast protein kinase C: Difference between the yeast and mammalian enzymes." J. Biochem. 112: 7–10.
Kaibuchi et al. (1989), "Molecular genetic analysis of the regulatory and catalytic domains of protein kinase C." J. Biol. Chem. 264: 13489–13496.
Knopf et al. (1986), "Cloning and expression of multiple protein kinase C cDNAs." Cell 46: 491–502.
Luo et al. (1993), "The regulatory domain of protein kinase C beta-1 contains phophatidylserin–and phorbol ester–dependent calcium binding activity." J. Biol. Chem. 268: 3715–3719.
Muramatsu et al. (1989), "A protein kinase C cDNA without the regulatory domain is active aftertransfection in vivo in the absence of phorbol ester." Mol. Cell. Biol. 9: 831–836.
Nishizuka et al. (1988), "The molecular heterogeneity of protein kinase C and its implications for cellular regulation" Nature 334: 661–665.
Ogita et al. (1990), "Protein kinase C in Saccharomyces cerevisiae: Comparison with the mammalian enzyme." Proc. Natl. Acad. Sci. USA 87: 5011–5015.
Ono et al. (1989), "Phorbol ester binding to protein kinase C requires a cysteine–rich zinc–finger–like sequence." Proc. Natl. Acad. Sci. USA 86: 4868–4871.
Parker et al. (1986), "The complete primary structure of protein kinase C—the major phorbol ester receptor." Science 233: 853–859.
Portillo et al. (1985), "Activation of yeast plasma membrane ATPase by phorbol ester." FEBS Lett. 192: 95–98.
Riedel et al. (1993), "Stimulation of calcium uptake in Saccharomyces cerevisiae by bovine protein kinase C α." J. Biol. Chem. 268: 3456–3462.
Riedel et al. (1993), "Phorbol ester activation of functional rat protein kinase C β–1 causes phenotype in yeast." Journal of Cellular Biochemistry vol. 52, No. 3, pp. 320–329.

(List continued on next page.)

Primary Examiner—John LeGuyader
Assistant Examiner—Andrew Wang
Attorney, Agent, or Firm—Louis Myers; Lahive & Cockfield

[57] ABSTRACT

A method evaluating the tumor promoter agonist or antagonist activity or the PKC activator or inhibitor activity of a compound. The method includes supplying a yeast cell expressing a PKC, contacting the yeast cell with a compound to be evaluated; and determining the value of a parameter related to tumor promoter agonist or antagonist or PKC activator or inhibitor activity in the cell, the effect of compound on the value of the parameter being indicative of the tumor promtoer or PKC activator or inhibitor activity of the compound.

15 Claims, 4 Drawing Sheets

OTHER PUBLICATIONS

Rotenberg et al. (1991), "Protein kinase C in neoplastic cells." In T.G. Pretlow II and T.P. Pretlow (eds.), *Biochemical and molecular aspects of selected cancers*, vol. 1, Academic Press, Inc., Orlando.

Simon et al. (1991), "The identification and purification of a mammalian-like protein kinase C in the yeast *Saccharomyces cerevisiae*." *Proc. R. Soc.* London B243: 165–171.

Su et al. (1993), "Functional carboxyl terminal deletion map of protein kinase C alpha." *Recept. Channels* vol. 1, No. 1, pp. 1–9.

Riedel et al. (1993) J. Cell. Biochem vol. 52: 320–329.

Riedel et al. (1993) J. Biol. Chem. vol. 268(5): 3456–3462.

Portillo et al. (1985) FEBS vol. 192(1): 95–98.

Osada et al. (1990) J. Biol. Chem. vol. 265(36): 22434–22440.

Osada et al. (1988) J. Antibiotics (Tokyo) vol. 41(7): 925–931.

Iwai et al. (1992) J. Biochem vol. 112: 7–10.

Ito et al. (1983) J. Bacteriol vol. 153(1): 163–168.

Kikkawa et al. (1987) FEBS Lett vol. 223(2): 212–216.

PROTEIN KINASE C ASSAY

This application is a continuation of U.S. Ser. No. 08/293,744, filed on Aug. 22, 1994, now abandoned, which is a continuation of U.S. Ser. No. 08/089,043, filed on Jul. 19, 1993, now abandoned.

BACKGROUND

The invention relates to the use of cells which express protein kinase C (PKC) for the evaluation of the tumor promoter agonist or antagonist function or the PKC activator or inhibitor function of a compound, or for the evaluation of the biological activity, e.g., the enzymatic activity, of a PKC.

The calcium- and phospholipid-dependent PKC family is ubiquitous in eukaryotes from yeast to man and plays important roles in the regulation of cell surface receptors, ion channels, secretion, neuronal plasticity and toxicity, and gene expression. CDNA sequence analysis of the gene family defines four highly conserved regions C1-C4, and five variable regions V1-V5, which vary between different subtypes. While the C1 region is critical for the regulation of PKC function and the C3-C4 regions for enzymatic activity, the roles of the C2 and the variable regions V1-V5 are less clearly defined.

Many isoforms are activated by diacylglycerol, phospholipids, and $Ca^{2+}$ in response to extracellular stimuli. PKC also plays a role in calcium mobilization including calcium uptake in various cell types. In addition, PKC is a major cellular receptor for tumor promoting and degradation resistant phorbol esters, which may cause protracted PKC activation which may ultimately result in tumor promotion. Consequently, PKC plays a growth stimulatory role in many mammalian cells while it has antiproliferative properties in others.

Potential members of the PKC family have been identified in other eukaryotes including yeast. In *Saccharomyces cerevisiae* a related diacylglycerol-stimulated but phorbol ester-unresponsive protein activity with distinct catalytic properties has been described, Ogita et al., 1990, *Proc. Natl. Acad. Sci. USA* 87: 5011 and Iwai et al., 1992, *J. Biochem* 112: 7, as well as putative mammalian-like PKC isoforms Simon et al., 1991, *Proc. R. Soc, Lond.* B243: 165. A related, essential gene, PKC1, has been identified in yeast with a role in osmotic stability and perhaps in bud morphogenesis, Levin et al., 1990, *Cell* 62: 213.

SUMMARY OF THE INVENTION

We have discovered that cells which are engineered to express a PKC acquire a tumor promoter-sensitive, PKC-related phenotype. The tumor promoter-sensitive phenotype, and in particular, a tumor promoter-induced alteration in the growth rate of the cells which express PKC, allow the cells to be used to in a relatively rapid, convenient, and inexpensive assay for evaluating the tumor promoter agonist or antagonist activity, or the PKC activator or inhibitor activity, of a compound e.g., a cosmetic or pharmaceutical product. Cells which express a PKC can also be used to evaluate the biological activity of the PKC, e.g., to evaluate the effect of a structural modification of a PKC on the PKC's biological activity.

Accordingly, the invention features, a method of evaluating the tumor promoter agonist or antagonist activity, or the PKC activator or inhibitor activity, of a treatment, e.g., the administration of a compound or other agent. The method includes: supplying a cell which expresses a PKC, preferably an exogenous PKC, e.g., a mammalian, e.g., a human, bovine, or rat PKC; administering the treatment, e.g., contacting the cell with a compound to be evaluated; and, determining the value of a parameter related to tumor promoter agonist or antagonist or PKC activator or inhibitor modulation of PKC, e.g., determining the growth rate of the cell. Tumor promoter agonist activity or PKC activator activity results in an increase in the growth rate of some cell types and a decrease in the rate of other cell types. The behavior of a cell type can be determined by administering a known tumor promoter agonist, e.g., PMA, a known tumor promoter antagonist, e.g., bryostatin or staurosporine, a known PKC activator, or a known PKC inhibitor, and determining the effect of the compound on the growth rate of the cell. In the case of *Saccharomyces cerevisiae*, a decrease in the growth rate of the cell is usually indicative of tumor promoter agonist or PKC activator activity and an increase in the growth rate of the cell, is usually indicative of tumor promoter antagonist or PKC inhibitor activity. PKC activators are substances which stimulate an enzymatic activity of PKC, e.g., kinase activity, some of which are also tumor promoters. PKC inhibitors are substances which inhibit an enzymatic activity of PKC, e.g., kinase activity, and may also inhibit tumor promotion. Tumor promoter agonists and antagonists can work in various ways. Tumor promoter antagonists, e.g., bryostatin, can activate PKC without resulting in tumor promotion. Other antagonists, e.g., staurosporine, can inhibit the enzymatic activity of PKC.

In preferred embodiments: the cell has no significant endogenous phorbol ester responsive PKC activity; the cell is a microbial cell; the cell is a lower eukaryotic cell; or the cell is a fungal cell, e.g., a yeast cell. In other preferred embodiments, the cell is a member of the Schizophyta; the cell is a member of the order Fucales; the cell is a member of the class Fungi; the cell is a member of the subclass Ascomycetes; the cell is a member of the subgroup Protoascomycetes, e.g., *Candida spec.*; the cell is a member of the order Saccharomycetales, e.g., Pichia spec.; the cell is a member of the family Saccharomycetaceal; the cell is a yeast of the genus Saccharomyces, e.g., *Saccharomyces cerevisiae*.

In other preferred embodiments the PKC is a one of the conventional PKC's, e.g., a PKC alpha, beta- 1, beta-2 or gamma; or the PKC is a novel PKC, e.g., PKC, delta, epsilon, zeta, or eta.

In another aspect, the invention features a method of evaluating the biological activity of a PKC, e.g., a mammalian PKC, e.g., a wild type, mutant, e.g., a deletion mutant, or otherwise modified PKC. By biological activity is meant any activity of the protein including: the ability to bind to a ligand, e.g., a tumor promoter agonist or antagonist, e.g., a phorbol ester or an agonist or antagonist of a phorbol ester, or an activator or inhibitor of PKC, e.g., calcium or phospholipids; the level of PKC enzyme activity, e.g., kinase activity; or the inducibility of a PKC enzyme activity, e.g., kinase activity. The method includes: supplying a cell which expresses a PKC, preferably an exogenous PKC, e.g., a mammalian PKC, e.g., a human, bovine, or rat PKC; contacting the cell with a compound having tumor promoter agonist or antagonist function; e.g., a phorbol ester, or with a compound having PKC activator or inhibitor function, and determining the value of a parameter related to tumor promoter agonist or antagonist or PKC activator or inhibitor modulation of PKC, e.g., determining the growth rate of the cell.

In *Saccharomyces cerevisiae*, the effect of the compound on the growth rate of the cell which expresses the PKC protein is indicative of the level of the biological activity of the PKC protein. Mammalian PKC activation in yeast results in PKC down regulation, phosphorylation of cellular proteins and stimulation of a specific extracellular calcium uptake mechanism similar to responses reported in mammalian cells. Since phorbol ester activation of mammalian PKC expressed in yeast results in a substantial increase in the cell doubling time (also observed in certain mammalian cells) this phenotype can be used in a systematic screen to identify functionally active random PKC deletion mutants e.g., directly on agar plates. Mutants screened by this technique can be used to map functions of the PKC domains and to define regions that interact with PKC tumor promoter activators and inhibitors such as anti-cancer drugs.

In preferred embodiments: the cell has no significant endogenous phorbol ester responsive PKC activity; the cell is a microbial cell; the cell is a lower eukaryotic cell; or the cell is a fungal cell, e.g., a yeast cell. In other preferred embodiments, the cell is a member of the Schizophyta; the cell is a member of the order Fucales; the cell is a member of the class Fungi; the cell is a member of the subclass Ascomycetes; the cell is a member of the subgroup Protoascomycetes, e.g., *Candida spec.*; the cell is a member of the order Saccharomycetales, e.g., Pichia spec.; the cell is a member of the family Saccharomycetaceal; the cell is a yeast of the genus Saccharomyces, e.g., *Saccharomyces cerevisiae*.

In other preferred embodiments the PKC is a one of the conventional PKC's, e.g., a PKC alpha, beta-1, beta-2 or gamma; or the PKC is a novel PKC, e.g., PKC, delta, epsilon, zeta, or eta.

In another aspect the invention features a method of determining the ability of a PKC, e.g., a mammalian PKC, e.g., a human, rat, or bovine PKC, e.g., a wild type, a mutant, e.g., a deletion mutant, or an otherwise modified PKC, to bind to a compound, e.g., a compound with tumor promoter agonist or antagonist activity, e.g., a phorbol ester, a phorbol ester agonist, or a phorbol ester antagonist, or a compound with PKC activator or inhibitor activity. The method includes: supplying a cell which expresses a PKC, preferably an exogenous PKC, e.g., a mammalian, e.g., a human, bovine, or rat PKC; contacting the cell with the compound; and, determining the value of a parameter related to tumor promoter agonist or antagonist, or PKC activator or inhibitor modulation of PKC, e.g., determining the growth rate of the cell. The ability of the expressed PKC to bind the compound is related to the parameter, e.g., it is related to an alteration in the growth rate of the cell.

In preferred embodiments: the cell has no significant endogenous phorbol ester responsive PKC activity; the cell is a microbial cell; the cell is a lower eukaryotic cell; or the cell is a fungal cell, e.g., a yeast cell. In other preferred embodiments, the cell is a member of the Schizophyta; the cell is a member of the order Fucales; the cell is a member of the class Fungi; the cell is a member of the subclass Ascomycetes; the cell is a member of the subgroup Protoascomycetes, e.g., *Candida spec.*; the cell is a member of the order Saccharomycetales, e.g., Pichia spec.; the cell is a member of the family Saccharomycetaceal; the cell is a yeast of the genus Saccharomyces, e.g., *Saccharomyces cerevisiae*.

In other preferred embodiments the PKC is a one of the conventional PKC's, e.g., a PKC alpha, beta-1, beta-2 or gamma; or the PKC is a novel PKC, e.g., PKC, delta, epsilon, zeta, or eta.

In another aspect, the invention features, a method of identifying a deletion or other lesion or modification of a DNA encoding a PKC. The method includes: mutagenizing DNA encoding a PKC; expressing the mutagenized DNA in a cell; contacting the cell with a compound having tumor promoter activity or PKC activator or inhibitor activity; and determining the effect of a modification induced by the mutagenisis on a tumor promoter agonist or antagonist or PKC activator or inhibitor-sensitive parameter, a change in the value of the parameter as compared to the value seen with a cell expressing wild type PKC being indicative of a modification.

In preferred embodiments: the cell has no significant endogenous phorbol ester responsive PKC activity; the cell is a microbial cell; the cell is a lower eukaryotic cell; or the cell is a fungal cell, e.g., a yeast cell. In other preferred embodiments, the cell is a member of the Schizophyta; the cell is a member of the order Fucales; the cell is a member of the class Fungi; the cell is a member of the subclass Ascomycetes; the cell is a member of the subgroup Protoascomycetes, e.g., *Candida spec.*; the cell is a member of the order Saccharomycetales, e.g., Pichia spec.; the cell is a member of the family Saccharomycetaceal; the cell is a yeast of the genus Saccharomyces, e.g., *Saccharomyces cerevisiae*.

In other preferred embodiments the PKC is a one of the conventional PKC's, e.g., a PKC alpha, beta-1, beta-2 or gamma; or the PKC is a novel PKC, e.g., PKC, delta, epsilon, zeta, or eta.

In other preferred embodiments: the PKC is a mammalian PKC, e.g., a human, rat, or bovine PKC; the tumor promoter agonist or antagonist or PKC activator or inhibitor -sensitive parameter is the rate of growth of the cell; the DNA is mutagenized prior to insertion in the cell; and the DNA is mutagenized after insertion into the cell.

PKC, as used herein, refers to both conventional PKC's, e.g., PKC alpha, PKC beta-1, PKC beta-2, and PKC gamma (the sequences of these PKC's are provided in Kikkawa et al., 1987, FEBS Lett. 223:212), as well as novel PKC's, e.g., PKC delta, PKC epsilon, PKC zeta, and PKC eta (the sequences of these PKC's are provided in Osada et al., 1990, J. Biol. Chem. 265:23,434 and references cited therein). Novel PKC's lack a C2 region. PKC's of the invention have protein kinase activity which can be activated by a phorbol ester, e.g., PMA or by diacylglycerol, phospholipids, or $Ca^{2+}$or a combination thereof. Conventional PKC's of the invention have C3 and C4 regions which are at least 40% homologous with, respectively, with the C3 and C4 regions of one or more of the conventional PKC's listed above. Novel PKC's of the invention have C3 and C4 regions which are at least 40% homologous with, respectively, the C3 and C4 regions of one or more of the novel PKC's listed above. The suitability of a PKC for use in the invention can be determined by expressing the PKC in a yeast, e.g., in *Saccharomyces cerevisiae*, and determining if it confers a tumor promoter sensitive phenotype, e.g., a reduction in growth rate in response to treatment with a tumor promoter, e.g., a phorbol ester, or a PKC activator or inhibitor sensitive phenotype, on the yeast cell. The references to domain nomenclature herein follow the usage of Kikkawa et al., 1987, supra.

The term, activity, as used herein includes both inhibitory and stimulatory activity.

Tumor promotor agonist, as used herein, refers to a substance which can act as a tumor promotor. Tumor promotor antagonist, as used herein, refers to a substance which inhibits or interferes with a tumor promotor agonist.

Exogenous, as used herein, refers to a gene or protein which is inserted into or expressed in a species other than the one it is found in nature.

We have established a microbial model for the evaluation of tumor promoter activity in a minimally complex system. The model is based in part on the fact that PKC isozymes, e.g. alpha and beta isozymes, are functionally expressed in the yeast *Saccharomyces cerevisia*, and that phorbol ester stimulation of yeast cells which express PKC leads to distinct biological responses corresponding to the distinct PKC isozyme characteristics seen in mammalian cells. As is discussed in detail below, bovine PKC alpha expression leads to a four-fold increase in the yeast doubling time and a resulting substantial decrease in yeast colony size on agar plates in response to phorbol ester activation, thus yeast cells which express PKC can serve as the basis of a rapid convenient, and relatively inexpensive phenotypic screen which permits the quantification of PKC activity and the identification of tumor promoter agonist and antagonist activity.

Carcinogenesis is a complex multistep process of initiation and promotion events. Phorbol esters, e.g., phorbol-12-myristate-13-acetate (PMA), and an established class of tumor promoters that are believed to act through cellular receptors which include the protein kinase C (PKC) family. Evaluation of tumor promoter activity has generally relied on whole animal models. Our screen provides an alternative approach which minimizes the use of animals. This microbial screen can be applied as an alternative to whole animal models to test any substance for tumor promoter activity. The basis of the yeast cell screen is the stimulation of mammalian PKC activity in yeast by tumor promoters and the resulting increase in the cell doubling time. Since small alterations of the yeast growth rate can be determined by yeast colony size on agar plates or in liquid culture, this screen can detect even weak activators or inhibitors of PKC. We have tested a variety of known tumor promoters (as defined in animal models) and have demonstrated that these substances modulate the yeast doubling time via PKC alpha in a proportional manner.

The system described herein can also be used to investigate the functional roles of the various structural domains of PKC and their interactions with various PKC ligands, e.g., PKC activator and inhibitors. When we expressed pools of randomly mutagenized bovine PKC alpha cDNAs in yeast we observed that the yeast colony size was inversely proportional to the mutant catalytic and physiological activities. This phenotype defines distinct classes of mutations based on PKC function and provides a rapid screen to isolate PKC mutants with altered enzymatic activities and ligand responses.

Other features and advantages of the invention will be apparent from the following description, the drawings, and the claims.

DETAILED DESCRIPTION

The drawings are first briefly described

DRAWINGS

Figure 1:
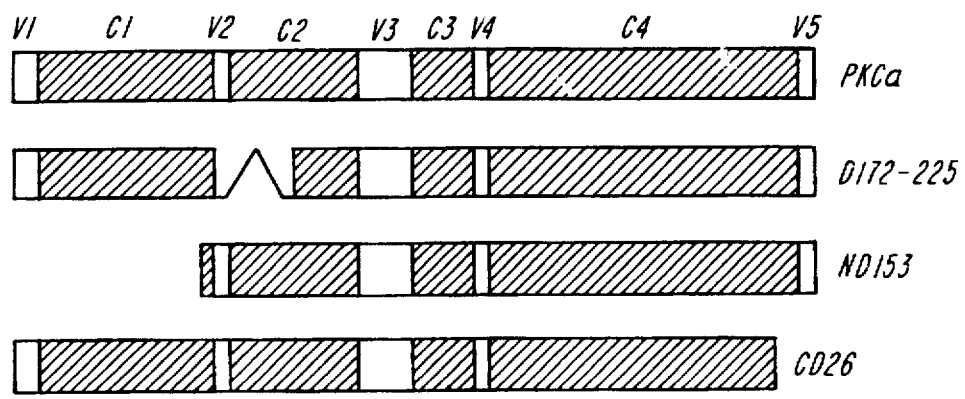

FIG. 1 is a diagram of the primary structure of PKC alpha wild type and mutant proteins. Deduced amino acid sequences of normal PKC alpha and deletion mutants D172-225, ND153 and CD26 have been aligned for maximum homology. Regions of constant (C1–C4) and variable (V1–V5) aa sequences between PKC subtypes are indicated by solid and open boxes, respectively. Deleted sequences have been omitted for emphasis or have been indicated by (^) for D172-225.

Figure 2:
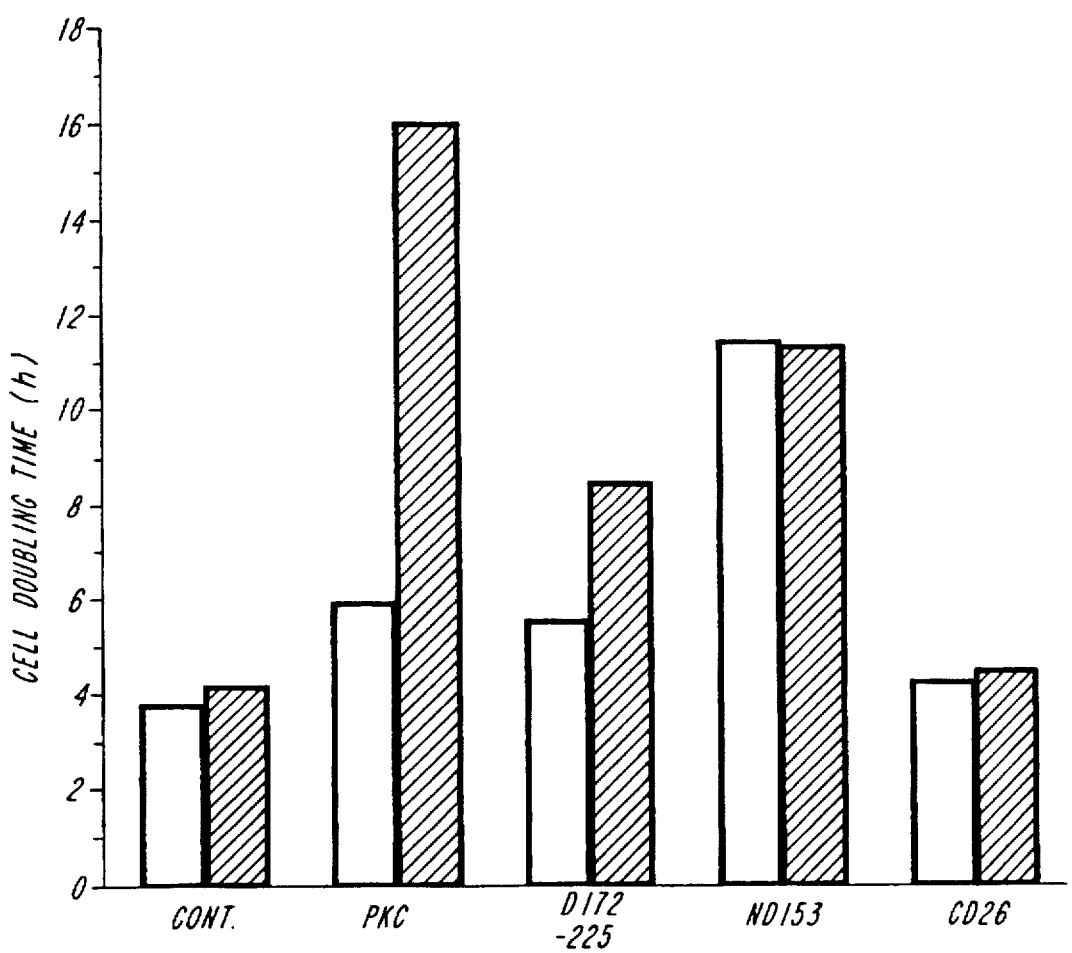

FIG. 2 is a graph of cell doubling time of yeast cultures expressing PKC alpha wild type and mutant cDNAs. Freshly saturated cultures expressing control plasmids (Cont.), normal PKC alpha (PKCa) or deletion mutants D172-225, ND153 or CD26 were diluted to low cell densities. Cell growth was followed on a roller at 30 degrees C to measurable cell densities of the logarithmic growth phase at 0.2–0.6 O.D. 600. The medium contained 2% galactose to induce cDNA transcription and 1 µM PMA (+PMA, solid) or the inactive isomer 4 alpha-PMA (−PMA, open). Average doubling times were calculated.

Figure 3:
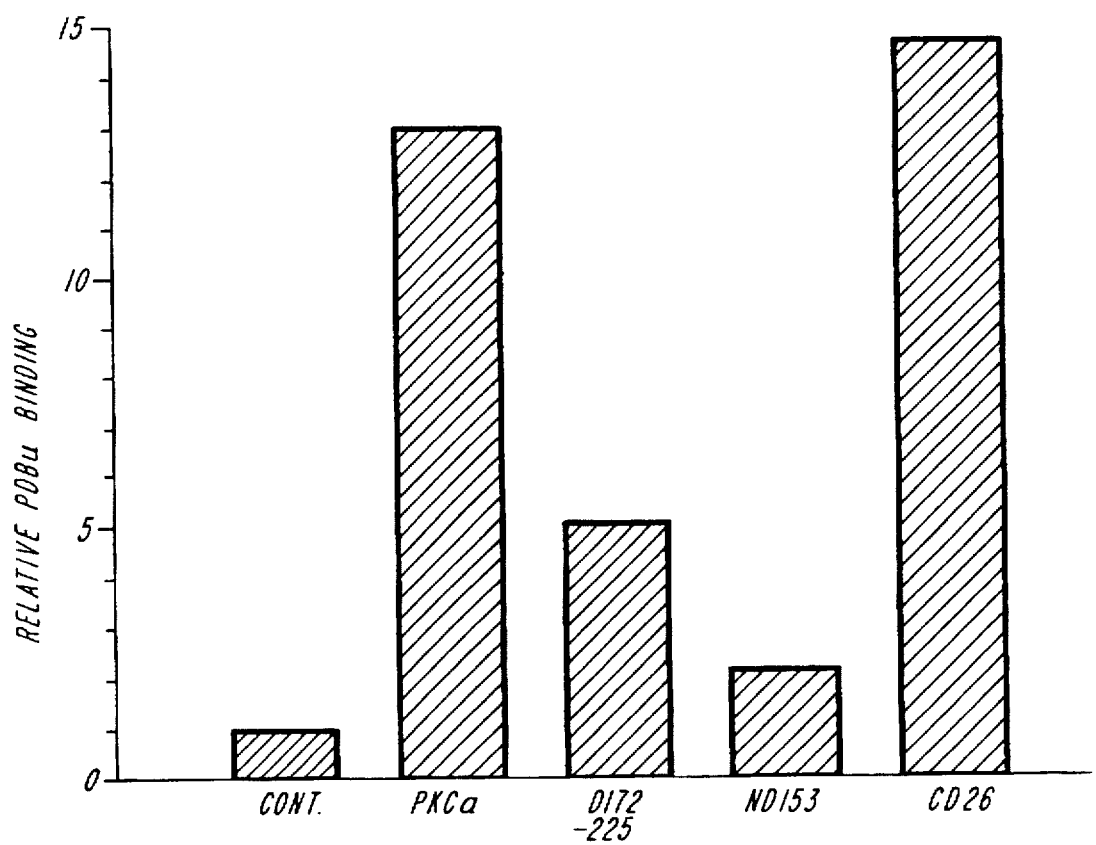

FIG. 3 is a graph of phorbol ester binding to cells expressing PKC alpha wild type and mutant proteins. [$^3$H]PDBu binding to yeast spheroplasts expressing control plasmids (Cont.), normal PKCa, or deletion mutants D172-225, ND153 or CD26, was compared.

Figure 4:
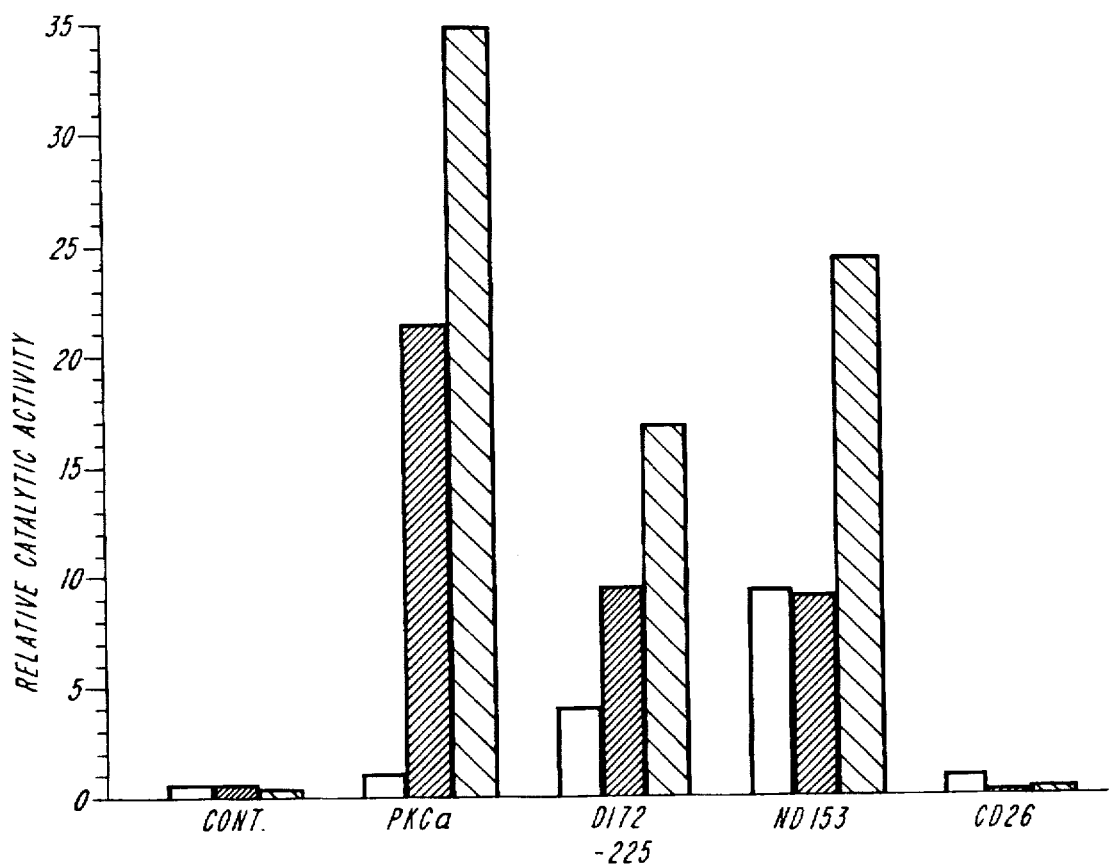

FIG. 4 is a graph which compares PKC mutant and wild type catalytic activities in vitro. Phosphorylation of the pseudosubstrate derivative |ser$^{25}$|PKC$_{19-31}$ was measured in detergent extracts of cells expressing control plasmids (Cont.), normal PKC alpha (PKCa) or deletion mutants D172-225, ND153 or CD26. Catalytic activity was stimulated by combinations of phosphatidylserine (PS), the phorbol ester PMA and calcium ions ($Ca^{2+}$). PS, open; PMA+PS, solid; $Ca^{2+}$+PS, diagonally striped.

Figure 5:
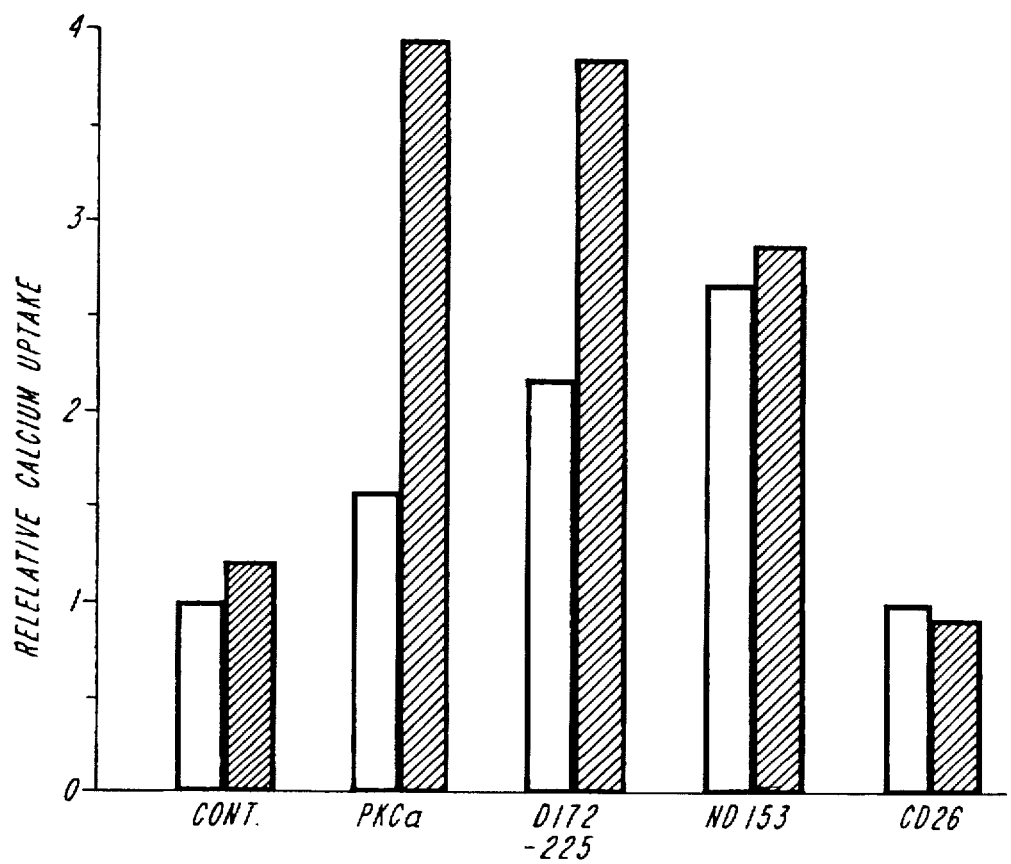

FIG. 5 is a graph of the modulation of extracellular Ca2+uptake by PKC alpha wild type and mutants. Yeast cells expressing control plasmids (Cont.), normal PKC alpha (PKCa) or deletion mutants D172-225, ND153 or CD26 were incubated with 45CaCl$_2$ to compare $Ca^{2+}$uptake in the presence of 1 µM PMA (+PMA, solid), or the inactive isomer 4 alpha-PMA (−PMA, open).

Materials and Methods

Duplicate measurements have routinely been made in our experiments. All tests have been independently performed several times with comparable results within a 10% error margin and representative data are shown. The methods described here are for the bovine PKC alpha experiments. The same or similar methods were used in the rat PKC beta-1 experiments.

Abbreviations. aa: amino acid; O.D.600: optical density at 600 nm; PBS: phosphate-buffered saline; PDBu: phorbol-12, 13-dibutyrate; PMA: phorbol-12-myristate- 13-acetate; PKCa: bovine protein kinase C alpha; D172-225: PKCa deletion of aa 172–225; ND153: PKCa deletion of aa 1–153; CD26: PKCa deletion of aa 647–672.

Yeast strains and culture conditions. PKC expression plasmids and YEp51 or YEp52 as controls were introduced into *Saccharomyces cerevisiae* strain 334 [MAT alpha, pep 4-3, prb1-122, ura 3-52; leu2-3, 112, reg1-501, gal1|by lithium acetate transformation See e.g., Ito et al. 1983, *J. Bacterial.* 153: 163. Cells were routinely grown at 30 degrees C on a culture roller or shaker in liquid culture or on 1.5% agar plates. The synthetic medium contained 2% glucose and was leucine-free to select for stable propagation of the expression plasmids. Expressing yeast colonies were identified phenotypically by replica plating on medium containing or lacking PMA. Phenol extracts of crude cell lysates were prepared to re-transform *Escherichia coli* DH5 alpha. PKC mutants were characterized by DNA sequencing and defined plasmids were re-introduces into *S. cerevisiae* 334. These strains were used in all experiments shown. 50 ml cultures were routinely inoculated from freshly saturated cultures and grown for 16 h to an optical density of 0.4 at O.D.600. Subsequently transcription of PKC cDNAs was routinely induced with 2% galactose for 3 hours except where indicated otherwise. This results in up to 700-fold induction of transcription in strain 334 within 3 hours. PKC activation was routinely measured in response to a single dose of 1 μM PMA or in controls (−PMA) in the presence of 1 μM of the inactive isomer 4 alpha-PMA (both available from LC Services, Woburn, Mass.) which were added at the start of each experiment.

PKC mutagenesis and cDNA construction. The complete protein-coding region of bovine protein kinase C alpha, see e.g., Parker et al., 1986, Science 233: 803–859, was joined at the NcoI site a the translation initiation codon with a synthetic A-rich HindIII - NcoI adapter 5'-AGCTTAAAAAA-3' (Seq. ID No. 1) and 3'-ATTTTTTGTAC-5' (Seq. ID No. 2) to optimize the sequence upstream of the ATG codon for improved translation efficiency. The cDNA was truncated at the 3' end by exonuclease Bal31 digestion and joined with a synthetic blunt end - XbaI adapter 5'-TAACTAACTAAT-3' (Seq. ID No. 3) and 3'-ATTGATTGATTAGATC-5' (Seq. ID No. 4) which provides translation stop codons in all three reading frames. A complete protein-coding cDNA including 10 base pairs of the 3' untranslated sequence was used for full-length PKC alpha expression (PKCa). To create the mutation CD26 a truncated cDNA lacking coding sequences for 26 carboxyl terminal aa (647–672) but containing a newly created asparagine codon was prepared. Both cDNAs were inserted into the HindII and XbaI sites under control of galactose-inducible GAL10 transcriptional elements of the high copy number yeast episomal expression plasmid YEp52 containing the LEU2 gene for selection. The mutation D172-225 lacking aa 172-225 was created by cleavage of the PKCa plasmid at a unique BamHI site, Bal31 digestion and re-ligation. To create the mutation ND153 lacking amino terminal aa 1–153, the PKC alpha cDNA was truncated from the 5' end by Bal31 digestion and a synthetic SalI –blunt end adapter 5'-TCGACAAAAAAAAAAATGGCT-3' (Seq. ID No. 5) and 3'-GTTTTTTTTTTTTACCGA-5' (Seq. ID No. 6) was joined to restore the methionine initiation codon and A-rich 5'-untranslated sequences for improved translation efficiency. The cDNA was inserted into the SalI and XbaI sites of YEp51 which differs form YEp52 only by various cloning sites. Using the same strategies additional deletion mutants were created lacking 84 (ND84), 118 (ND118), 140 (ND140) or 158 (ND158) amino terminal aa, lacking 96 (CD96), 110 (CD 110), 139 (CD139) or 149 (CD149) carboxyl terminal aa or lacking internal aa as specified by their position number D186 –189;, D156–234 or D149–240 (See Table 1). Methionine initiation codons had been restored in ND140, ND153, methionine and alanine codons in ND84, ND 118, ND158 and leucine, threonine and asparagine codons at the carboxyl terminus of CD149. After ligation all plasmids were amplified in *Escherichia coli* DH5 alpha and were identified and confirmed by restriction analysis and DNA sequencing.

Phorbol ester binding. About 6×10$^8$ expressing cells were washed twice in 10 mM K-phosphate buffer pH 7.0, 20 mM EDTA, once in 1M sorbitol and were resuspended in 10 ml 10 mM K-phosphate buffer pH 7.0, 1.1M sorbitol, 0.5 mM CaCl$_2$. Cells were incubated with 1 U glusulase (beta-glucuronidase/arylsulfatase from *Helix pomatia*, Boehringer Mannheim) for about 1 hour under shaking at 30 degrees C to remove the cell wall until test cell suspensions cleared in H$_2$O due to cell lysis. 1.5×10$^8$ spheroplasts were incubated in 15ml tubes in 1 ml 2% glucose, 2% galactose, 1.1M sorbitol, 1 mg/ml BSA, 75 mM Hepes pH 7.4 at 30 degrees C for 90 min. with 14 nM [3H]PDBu at 25 Ci/mmol (Amersham) and nonspecific binding was determine in the presence of 20 μM of unlabeled PDBu, 1M sorbitol, 50 mM Hepes pH 7.4 and the cell-associated radioactivity was determined by liquid scintillation spectroscopy. Highest PKC levels resulted in specific binding of 5% of the [$^3$H] PDBu in the experiment.

Cell lysis. About 6×10$^8$ expressing cells were washed in PBS and were resuspended in 1 ml lysis buffer containing 1% Triton X100, 50 mM Hepes pH 7.4, 15-mM NaCl, 5 mM EDTA, 5 mM EGTA, 10 μg/ml pepstatin, 40 μg/ml leupeptin, 10 μg/ml aprotinin and 200 μg/ml PMSF. Cell suspensions mixed with the same volume of acid washed glass beads (450-500 μm) were lysed mechanically by six 30 second vortexing steps interrupted by cooling on ice for at least 30 second in 50 ml screw cap polypropylene tubes. The lysate was cleared by 4,000 g centrifugation for 15 minutes at 4 degrees C and stored at ×70 degrees C for up to several weeks.

PKC catalytic activity. PKC catalytic activity was measured as described in Hu et al., 1990, *J. Biol. Chem.* 265: 13864 by phosphorylation of 3 μg of the specific substrate peptide RFARKGSLRQKNV (Seq. ID No. 7) (Gibco, BRL) in the presence of 5 μCi [gamma-32P]ATP (3000 Ci/mmol) in 125 μl of 5-fold diluted cell extract for 30 min. at 25 degrees C with combinations of 160 μg/ml phosphatidylserine (Avanti Polar Lipids, Inc.), 1 μm PMA and 5 mM CaCl$_2$. Phosphatidylserine in chloroform, with or without PMA was evaporated under N$_2$ to dryness, resuspended in 20 mM Tris pH 7.5, mixed and sonicated at 4 degrees C for 45 seconds before use. To terminate the reaction the sample was placed on phosphocellulose paper (Whatman P81) which was repeatedly washed in 75 mM phosphoric acid. Bound radioactivity was determined by liquid scintillation spectroscopy.

$^{45}$Ca$^{2+}$ uptake. Expressing yeast cells after 16 h in 2% galactose medium were washed with PBS when reaching 0.5 O.D.600. 10$^7$ cells were suspended in 100 μl of 50 mM MES pH 6.5, 5 mM MgSO$_4$ and incubated with 1 μM PMA for 1 h at 30 degrees C under shaking on 96-well plates. Subsequently uptake of 2 μCi 45 Ca2+ at 300 μM CaCl2 was measured for 2 hours. Cells were rapidly transferred to Multiscreen filtration microtiter plates (Millipore) and washed four times with 200 μl of 10 mM MES, 10 mM Tris, 35 mM CaCl2 pH 6.0. Filters were dried and cell-associated radioactivity was determined by liquid scintillation spectroscopy.

Expression of normal bovine PKC alpha resulted in a four-fold increase in the cell doubling time and substantially reduced yeast colony size when compared to wild-type yeast cells.

Full length and mutant PKC coding regions were expressed in *Saccharomyces cerevisiae*. To create bovine PKC alpha mutations with random alterations in major protein coding domains we prepared cDNA deletions internally within the C1, V2 and C2 coding regions and from the amino terminal and carboxyl terminal coding regions by exonuclease Bal31 digestion as shown for three examples in FIG. 1. PKC cDNAs were introduced into the high copy number episomal yeast expression plasmids YEp51/52 under control of galactose-inducible transcriptional element. Pools of plasmids were amplified in *E. coli* and purified for yeast transformation. Yeast colonies were screened on agar plates in the presence of 2% galactose to induce maximal cDNA transcription and of 1 μM phorbol ester phorbol-12-myristate- 13-acetate (PMA) to stimulate PKC cataltic activity, see castagna et al., 1982, *J Biol. Chem.* 257: 7847. Under these conditions, expression of normal bovine PKC alpha resulted in a four-fold increase in the cell doubling time (FIG. 2) and substantially reduced yeast colony size when compared to wild-type yeast cells which did not respond to PMA.

Mutant PKC alpha expression and phenotype

Most of the yeast cells transformed with random PKC alpha cDNA deletions were expected to express inactive PKC fragments and indeed most displayed a wild-type yeast phenotype. However 1% of colonies transformed with internal or amino terminal PKC deletions were reduced in size to various degrees in response to PMA by comparison to replica plated colonies on PMA-free control plates. These colonies were chosen as candidates for the expression of functional PKC forms with varying enzymatic activities and ligand responses. In contrast transformation with carboxyl terminal PKC truncations normally resulted in the wild-type yeast phenotype.

The phenotypic screen of PKC alpha mutant activity by yeast colony size was performed as follows. Freshly saturated yeast cultures expressing control plasmids (Control), normal PKC alpha (PKCa) or deletion mutants D172-225, ND 153 or 26 aa were diluted and comparable cell numbers were spread on agar plates. Colonies were grown at 30 degrees C in the absence −GAL.) or presence (+GAL.) of 2% galactose to induce cDNA transcription and in the presence of 1 uM PMA (+PMA) or the inactive isomer 4alpha-PMA (−PMA). Plates (9 cm diameter) were photograph after 3 days.

Primary structure of PKC alpha mutants.

Representative yeast colonies of each of the three types of PKC deletions were isolated, grown to saturation in liquid culture, diluted, spread on agar plates and one example for each type is shown under various conditions described above. To determine the exact primary structure of the deletion mutants, plasmids from crude extracts of expressing yeast cells were introduced into *E. coli* and amplified plasmids were purified and sequenced. All experiments in this study were performed with *Saccharomyces cerevisiae* strain 334 which had been re-transformed with these defined plasmids. The deduced primary structures for the presented examples are compared in FIG. 1. The internal deletion is lacking aa 172–225 comprising the amino termninal half of the PKC C2 domain which is not essential for phorbol ester stimulation of PKC activity. The amino terminal truncation is lacking 153aa including the V1 and most of the C1 domain, in particular all 12 cysteine residues involved in phorbol ester binding and the pseudosubstrate sequence with is expected to inhibit the catalytic activity in the absence of activator. This structure explains the phorbol ester-independent, elevated basal activity of this mutant. The carboxyl terminal truncation is lacking 26aa (647 –672) including the V5 and the end of the catalytic C4 domain which results in inactivation of the kinase and explains the lack of PKC activity and the resulting normal yeast phenotype.

Yeast phenotype in response to PKC alpha expression.

On galactose-free plates all transformants displayed the wild-type phenotype which was unaffected by PMA (as expected in the absence of cDNA transcription). Galactose stimulation of cDNA expression resulted for some PKC forms in specific, decreased yeast colony sizes which were either dependent on or independent of phorbol ester activation after 3 days. Normal PKC alpha expression caused reduced colony sizes which were substantially further decreased to microscopically small sizes by phorbol ester activation. Internal PKC deletions such as D172-225 resulted in only slightly reduced colony sizes which were further decreased by phorbol ester stimulation to sizes slightly smaller than PKC alpha-expressing colonies in the absence of phorbol ester. Amino terminal truncations such as ND153 led to microscopically small colonies independent of phorbol ester activation. Carboxyl terminal truncations such as CD26 as well as control plasmids resulted in the wild-type phenotype under any condition. Microscopically small colonies expressing ND153 grew to visible sizes with rates independently of PMA. Colonies expressing PKC alpha grew even more slowly to visible sizes during continued incubation in the presence of PMA. Colony numbers were comparable in all experiments indicating that yeast viability is not affected by any of the PKC forms.

PKC alpha dependent modulation of yeast doubling time correlates with colony size.

Cell doubling times were measured by O.D.600 reading of liquid cultures in the presence of 2% galactose as shown in FIG. 2 to test whether they correlate with the specific phenotypes (colony size) caused by normal mutant PKC alpha. Control plasmids or carboxyl terminal PKC truncations such as CD26 resulted in an average cell doubling time of 4 hours in synthetic minimal medium which is normal for the employed *Saccharomyces cerevisiae* strain 334 and remained unaffected by phorbol ester. In the absence of phorbol ester normal PKC alpha and the internal deletion D172-225 cause a 50% increase in the cell doubling time to 6 h while amino terminal truncations such as ND153 resulted in a phorbol ester-independent 3-fold increase to 12 h. Phorbol ester stimulation of the internal deletion mutant and normal PKC alpha resulted in 2-fold and 4-fold increases in the cell doubling time to 9 hours and 16 hours, respectively. A normal 4 hours doubling time was measured for all constructs in the absence of galactose. Our data indicate a clear correlation between the specific yeast colony sizes on agar plates and the cell doubling time, both of which are differentially modulated by normal PKC alpha and mutant PKC classes.

Protein gel analysis of PKC mutants.

To test whether protein products of the predicted sizes were properly synthesized, detergent extracts of expressing cells were separated on SDS polyacrylamide gels and proteins were analyzed with PKC alpha-specific antibodies in immunoblots. PKC alpha was found to co-migrate at 80 k MW with PKC isolated from rat brain and the PKC deletions D172-225 and CD26 were detected as major protein bands of 70 k and 75 k MW, respectively, consistent with their predicted sizes and with proper protein expression. ND153 resulted in two major bands of 60 k and 65 k MW. The lower 60 k band was consistently more prominent and most closely corresponds to the predicted size of the protein based on the deletion of 153aa. This heterogeneity which has not been investigated may be due to different levels of PKC phosphorylation which have been shown in mammalian cells. Since whole cell extracts had directly been loaded on SDS gels without further purification, protein signals were low. Similar band intensities were reproducibly observed on nitrocellulose filters for normal PKC alpha and the 60 k (lower) band of ND153 which suggest comparable expression levels consistent with comparable PKC activities described below. Similar expression levels of normal PKC alpha and CD26 are also suggested by phorbol ester binding data in FIG. 3 while band intensities of D72-225 were typically slightly reduced in immunoblots.

Western blot of PKC alpha mutants expressed in yeast were performed as follows. Detergent extracts of yeast cells expressing control plasmids, normal PKC alpha or deletion mutants D72-225, ND153 or CD26 were separated on 8% SDS polyacrylamide gels. Proteins were transferred to nitrocellulose and analyzed with specific antibodies to mammalian PKC alpha in immunoblots.

In vivo phorbol ester binding activity of PKC alpha expressed in Saccharomyces.

To directly test the function of the regulatory PKC domain, phorbol ester binding sites were determined after enzymatic removal of the yeast cell wall by exposure of yeast spheroplasts to [$^3$H]phorbol-12, 13-dibutyrate ([$^3$H]PDBu). A comparison of normal PKC alpha and PKC mutants in FIG. 3 showed similar [$^3$H]PDBu binding levels for normal PKC alpha and CD26. Both were about 13-fold elevated over background levels of control cells. Similar findings have been reported for PKC overexpression in transfected mammalian fibroblasts. The removal of the C-terminal 26aa does not appear to affect PKC phorbol ester binding activity. In contrast the amino terminal 153aa truncation resulted in virtually background [$^3$H]PDBu binding levels, consistent with the expected loss of the phorbol ester binding domain by this mutation. The internal deletion of aa 172–225 led to phorbol ester binding levels reduced by 60% compared to normal PKC alpha, a potential consequence of the removal of parts of the C2 domain.

In vitro catalytic activity of PKC alpha mutants.

To test whether the distinct phenotype of expressing yeast cells correlates with the catalytic activity of the PKC forms expressed, phosphorylation of the PKC-specific substrate |ser25|PKC 19-31, a derivative of the pseudosubstrate sequence see, House et al. 1987, *Science* 238: 1726, was measured in detergent cells extracts in response to combinations of phosphatidylserine, PMA and calcium. As shown in FIG. 4, no activity was detected under any conditions for CD26 consistent with the inactivation of the kinase by the carboxyl terminal 26aa truncation. In the presence of phosphatidylserine alone no catalytic activity was detected for normal PKC alpha while D172-225 displayed 4-fold and ND153 10-fold elevated levels. This suggests partial and significant elevation of their basal catalytic activities, respectively, as a consequence of the structural changes. Phorbol ester treatment of normal PKC alpha resulted in more than 20-fold stimulation of catalytic activity compared to a 2-fold stimulation of D172-225. This indicates reduced responsiveness of D172-225 reduced phorbol ester binding (FIG. 3). The catalytic activity of ND 153 was PMA-unresponsive consistent with the loss of the phorbol ester binding domain in this mutant. Maximal catalytic activity of all three active PKC forms was stimulated by calcium—one of the basic characteristics of PKC. The catalytic activities of the mutants, elevated basal activity of ND153, full and reduced phorbol ester-stimulated activity of normal PKC alpha and D172-225, respectively, and lack of activity for CD26, clearly correlate with the sizes of expressing yeast colonies.

$Ca^{2+}$uptake mediated by PKC alpha expression.

$Ca^{2+}$influx has been reported in response to PKC activation in a variety of eukaryotic cells such as *Nitella syncarpa* plasmalemma, Aplysia bag cell neurons, rat ventricular myocytes and rat pituitary cells. To test whether the measured catalytic activities and the yeast phenotype correlate with other biological responses mediated by PKC, $^{45}Ca^{2+}$ uptake into expressing cells was determined after PMA stimulation. As shown in FIG. 5, CD26 displayed the same basal response as control cells which was unaffected by phorbol ester and is consistent with the lack of PKC enzymatic activity caused by the carboxyl terminal truncation. Normal PKC alpha displayed a 1.4-fold, D172-225 a 2-fold and ND153 an almost 3-fold increase in $Ca^{2+}$uptake, which are overall comparable with basal catalytic and yeast phenotypic responses for these PKC forms. Stimulation of $Ca^{2+}$ uptake by ND153 was unaffected by phorbol ester consistent with its constitutive catalytic activity and the resulting yeast phenotype. After PMA stimulation of normal PKC alpha or D172-225, Ca2+uptake increased to levels up to 4-fold over the control cell background suggesting almost comparable maximal responses for both PKC forms. These responses are consistent with the catalytic activities and phenotypic responses of the mutants: elevated basal activity of ND153, full and reduced phorbol ester-stimulated activity of normal PKC alpha and D172-225, respectively, and lack of activity for CD26.

Levels of PKC activity correlate with observed catalytic and biological responses.

Overall the distinct levels of PKC activity observed for wild type and the different mutants tested correlate well between catalytic and biological responses. Some existing variations are not unexpected when comparing experiments performed in different time frames and under widely varying in vivo and in vitro conditions. The high phorbol ester-stimulated $Ca^{2+}$uptake observed for the internal deletion D172-225 could be explained by different time dependencies of protein expression or altered down regulation compared to normal PKC alpha which has not been addressed. The reduced phorbol ester binding of D172-225 when compared to normal PKC alpha may be a consequence of lowered phorbol ester affinity which has been reported for one but not for another PKC alpha mutant both of which carry deletions in the C2 domain. We have identified and classified additional mutations with the phenotypic screen as shown in Table 1 which fall into the same three distinct functional classes. Enzymatic activities were measured in vitro in response to PMA and $Ca^{2+}$ and modulation of the cell doubling time was compared in vivo in response to PMA. Catalytic and biological responses correlated well and have been indicated by a common symbol in Table 1.

TABLE 1

PMA and $Ca^{2+}$ stimulated mutant PKC activity

|  | − | PMA | $Ca^{2+}$ |
|---|---|---|---|
| PKC alpha | − | ++ | ++ |
| ND84 | + | + | ++ |
| ND188 | + | + | ++ |
| ND 140 | + | + | ++ |
| <u>ND153</u> | + | + | ++ |
| ND158 | + | + | ++ |
| D186–189 | (−) | + | + |
| <u>D172–225</u> | (−) | + | + |
| D156 . 234 | (−) | + | + |
| D149–240 | (−) | + | + |
| <u>CD26</u> | − | − | − |
| CD96 | − | − | − |
| CD110 | − | − | − |
| CD139 | − | − | − |
| CD149 | − | − | − |

Additional PKC deletion mutants representing three distinct functional classed as listed above were tested for PMA and $Ca^{2+}$ stimulation of in bitro catalytic activity and PMA-mediated increase of the cell doubling time as shown in detail in FIGS. 4 and 2, respectively for the doubl-underlined mutants. Both in vitro and in vivo responses to PMA correlated well and all activities measured are represented by the following symbols (with increasing levels: −, (−), + or ++.

PKC amino terminal truncation mutants. Amino terminal truncations of 84 to 158aa are lacking the V1 and between the first half and most of the C1 region. All display a significantly elevated basal level of PKC activity. This is not unexpected after removal of the pseudosubstrate sequence which has been studied by proteolysis and cDNA mutagenesis. All mutants are unresponsive to phorbol esters consisted with the predicted role of the cysteine repeats in the C1 region in phorbol ester binding. The enzymatic activity of these mutants is still responsive to $Ca^{2+}$ which suggests that sequences in the C2 region or in the catalytic domain are responsible for this function which has not been accurately mapped to this date. Internal, amino terminal, and carboxy terminal mutants are disclosed below.

PKC internal deletion mutants. Internal PKC deletions lacking between 4 and 92aa including the V2, 60% of the C2 and little of the C1 region (D186–189 to D149–240) have been identified as shown in Table 1. All forms are still regulated by phorbol ester and $Ca^{2+}$ while their maximum enzymatic activities are reduced compared to normal PKC alpha. Our finding suggest that deletion of more than 90aa from the PKC regulatory domain is compatible with the basic functional characteristics of PKC alpha. The somewhat elevated basal level may suggest a potential role of amino terminal sequences in the C2 domain in the regulation of the kinase, a question which has not been addressed in reports of other PKC C2 domain deletions (24,5). These sequences appear not to be essential for PKC activation and in particular not for Ca2+binding.

PKC carboxyl terminal truncation mutants. All carboxyl terminal truncations identified, ranging from CD26 to CD 149 resulted in inactive proteins as shown in Table 1. These data indicate that PKC alpha enzymatic activity is lost after minimal truncation of the C4 region. Catalytic activity is not restored by increasing deletions suggesting that essential catalytic sequences may have already been affected by a small truncation. In CD26 catalytic activity is already lost although none of the putative autophosphorylation sites has been removed as based on autophosphorylation studies of PKC betaII.

Homologous PKC action in yeast and mammals.

Mammalian PKC plays a growth stimulatory role in many mammalian cells but has antiproliferative properties in other cell types including yeast, as shown in this study. While putative mammalian PKC-like protein activity has been reported in yeast Simon et al., 1991, *Proc. R. Soc. Lond.* B 243: 165, we have not found any evidence for PMA stimulated yeast PKC activity in any of our assays. This is consistent with the characteristics of the originally reported yeast PKC protein activity which does not significantly respond to phorbol esters and displays altered substrate specificity compared to mammalian PKC. Ogita et al., 1990, *Proc. Natl. Acad. Sci. USA*87: 5011 and Iwai et al., 1992, *J. Biochem.* 112: 7. The clear correlation between phorbol ester activation of PKC and the specific responses measured in various assays in this study compared to control cells indicate that the phenotypic screen quantifies mammalian PKC activity in the presently undefined yeast cellular background. Our results show that mammalian PKC expression confers a dramatic phorbol ester response on yeast while only subtle physiological consequences have been reported in wild-type yeast cells. Portillo et al., 1985, *FEBS lett.* 192: 95–98. Thus, phorbol esters are able reach and activate their target receptors in yeast. A gene (PKC1) with a role in osmotic stability has been identified in yeast which shares 53% and 51% amino acid identity with rat PKC beta 1 and gamma, respectively. PKC1 and extragenic suppressors of the BCK1 or SKCd locus may participate in the same pathway with a putative function in the cell cycle, perhaps in bud morphogenesis. PKC1 may play a role in the regulation of a protein kinase cascade where the BCKI gene product activates a pair of protein kinases encoded by the MKK1 and MKK2 genes which are homologs of mammalian mitogen-activated (MAP) kinase-kinase. This is believed to result in the activation of a yeast homolog of mammalian MAP kinase which is encoded by the MPK1 gene.

rat PKC beta-1 expression in yeast.

When rat PKC beta-1 was inserted into yeast it conferred a phorbol ester receptor phenotype on yeast cells. To create yeast expression constructs we inserted the complete protein coding cDNA of rat PKC β-1 (Housey et al., 1987, *Proc Nat'l. Acad. Sci. USA*84: 1065, under the control of galactose-inducible GAL10 transcriptional promoter element into the high copy number episomal plasmids YEp51. In addition two controls, truncation mutants lacking 12 amino terminal or 15 carboxyl terminal amino acids (aa) were prepared by Bal31 exonuclease treatment and were named ND12 or CD 15, respectively. Plasmids were stably propagated in transformed *S. cerevisiae* strain334 by selection in leucine free 2% glucose medium and transcription was routinely induces with 2% galactose for 18 hours in most experiments. Control YEp51 -transformed cells were used to determine the experimental background.

To test whether normal and truncated PKC beta-1 protein products of the predicted structures are properly expressed, detergent extracts of transformed cells were separated on SDS polyacrylamide gels and proteins were analyzed in immuno blots with PKC-specific antibodies. Expression of normal PKC β-1 resulted in a single antigenic protein band of 80 k MW which comigrated with PKC isolated from rat brain. Expression of PKC truncation mutants CD15 and ND12 resulted in a single protein band of 78 k or 75 k MW, respectively. As expected substantial changes in migration are not observed at this level of resolution due to the small truncations by 15 and 12aa, respectively. However the ND12 protein band consistently migrated faster than the CD 15 protein, suggesting that truncation of the PKC amino terminus and carboxyl terminus result in distinct changes in protein migration of SDS polyacrylamide gels which do not strictly correlate with the extent of the truncation in a linear fashion. The predicted primary structures of both truncation mutants had been confirmed by cDNA sequencing. Expression levels and/or stabilities of normal and truncated PKC forms appear to be overall comparable based on band intensities on the original immuno blot of cell extracts and based on similar levels of phorbol ester binding to expressing yeast cells in vivo.

To directly test the function of the regulatory PKC domain, phorbol ester binding sites were determined after enzymatic removal of the yeast cell wall by exposure of yeast spheroplasts to [$^3$H]phorbol- 12, 13-dibutyrate (|$^3$H| PDBu). Expression of normal PKC β-1 resulted in |$^3$H| PDBu binding levels which were more than 10-fold elevated over background levels of control transformed yeast cells as observed upon PKC expression in transfected mammalian fibroblasts. Truncation of the amino terminus by 12aa or of the carboxyl terminus by 15 aa as represented by the mutants ND 12 and CD15, respectively, resulted in similar PDBu binding activity. These data suggest that the truncations do not interfere with the function of the PKC regulatory domain and that expression levels are comparable between the different PKC forms. Scatchard analysis suggested $0.5 \times 10^4$ PDBu-binding sites per yeast cell (10 µm diameter) with a low affinity of 80 nM $K_d$ for normal PKC β-1. PKC expression levels in yeast appear to be somewhat lower than in the richest mammalian PKC sources (such as rat brain) but overall in the same order of magnitude as in many mammalian cells.

To compare the enzymatic activity of normal and truncated PKC forms, phosphorylation of the PKC-specific substrate [ser$^{25}$]PKC$_{19-31}$ a derivative of the pseudosubstrate sequence was measured in detergent cell extracts in response to combinations of phosphatidylserine, the phorbol ester PMA (phorbol-12-myristate-13-acetate), and $Ca^{2+}$. In the presence of phosphatidylserine alone only a background level of phosphorylation was detected in all samples including control cells which likely represents the activity of other endogenous yeast protein kinases. A 7-fold or 4-fold stimulation was measured after the addition of calcium and a 3-fold or 2.5-fold increase was observed after PMA stimulation for normal PKC β-1 Catalytic activity was phospholipid dependent and was stimulated by diacylglycerol similar to PMA. Our findings with ND12 indicated that while maximum catalytic activity is somewhat reduced by truncation of 12 amino terminal aa, this mutation is still compatible with a calcium- and phospholipid-dependent and phorbol ester-responsive enzymatic activity and shares the basic catalytic characteristics of PKC β-1. Truncation of 15 carboxyl terminal aa in CD15 however results in undetectable levels of enzymatic activity suggesting that sequences essential for catalytic PKC activity have been affected.

To measure PKC β-1 catalytic activity in vivo, expressing cells were metabolically labeled with 32P and nuclei-enriched cell fractions from Ficoll step gradients were analyzed on SDS polyacrylamide gels. While the pattern of most yeast phosphoproteins did not change, a protein band of 15 k MW was detected after PMA stimulation of PKC β-1 which was not visible in control cells. A comparable phosphoprotein was detected albeit weakly in whole cell extracts suggesting that the phosphorylated 15 k protein may be a yeast nuclear protein. Our data indicate catalytic PKC β-1 activity in vivo and the presence of yeast protein substrates which may be responsible for the observed biological responses.

To test whether the enzymatic activities observed for normal and truncated PKC β-1 forms correlate with biological responses mediated by PKC, $^{45}Ca^{2+}$ uptake into expressing cells was determined after PMA stimulation. CD15 displayed the same basal response as control cells which was unaffected by phorbol ester and is consistent with the lack of PKC enzymatic activity caused by the carboxyl terminal truncation. Normal PKC β1 and ND12 both displayed as almost two-fold increased level of $Ca^{2+}$ uptake which corresponds to the in vitro enzymatic properties of these PKC forms and suggests an overall correlation between PKC catalytic and biological activities.

When we investigated the effect of PKC β1 on the doubling time of expressing yeast cells we observed an almost three-fold increase upon phorbol ester activation which was reversible and did not affect cell viability. A similar response was measured for ND12 while CD15 resulted in cell doubling times indistinguishable from control transformed cells. Our data show a correlation between two biological responses, $^{45}Ca^{2+}$ uptake and modulation of the yeast cell doubling time for all PKC forms and suggest that while deletion of 12 amino terminal aa still allows virtually normal biological PKC β-1 and ND12 caused a phenotype represented by string-like cellular structures. This phenotype has not been well established in yeast and does not offer an obvious explanation for the underlying molecular mechanism which remains to be elucidated by further studies. However this response suggests phorbol ester-stimulated activity of normal PKC β-1 and ND12 and loss of function for CD15 consistent with the other enzymatic and biological functional assays described above.

Our findings indicate that normal and amino or carboxyl terminal truncation mutants of rat PKC β-1 are faithfully synthesized in yeast and result in cellular phorbol ester binding sites. Expression products display substrate-specific calcium-, phospholipid-, and phorbol ester-responsive enzymatic activity in cell extracts, phosphorylate yeast proteins in vivo, and result in proportional biological consequences. Three response which were measured in vivo: $^{45}Ca^{2+}$ uptake, the modulation of the cell doubling time, and the altered cell morphology all correlate well with the enzymatic activities measured in vitro. Compared to normal PKC β-1 truncation of 12 amino terminal aa (ND12) resulted in somewhat reduced enzymatic but normal biological activity. Enzymatic properties were calcium-, phospholipid-, and phorbol ester-responsive and display the basic characteristics of PKC β-1 while truncation of 15 carboxyl terminal aa (CD 15) results in loss of enzymatic and biological activity. Further carboxyl terminal truncation consistently results in inactive proteins and does not restore PKC enzymatic activity which has been tested for PKC β-1 mutants lacking 18, 32, 42, 56, and 67 aa.

Our findings indicate that the amino terminal 12 aa of PKC β-1 are not essential for PKC function while removal of 15 carboxyl terminal aa results in loss of PKC enzymatic activity. This defines the boundary of the region essential for PKC β-1 enzymatic activity within 15 aa from the carboxyl terminus based on functional criteria.

Overall PKC activities correlate well between enzymatic and biological responses and the truncation mutants. While biological responses to ND12 are comparable to normal PKC β-1 its catalytic activity appears to be lowered by one quarter compared to normal levels. Enzymatic in vitro studies may not always properly reflect in vivo PKC function or full biological responses may be reached with somewhat reduced enzymatic activity. The PKC β-1 amino terminus may enhance the enzymatic activity and perhaps benefit the conformation or stability of the protein. Serine an threonine autophosphorylation sites have been determined in the V1, V3, and C4 regions of PKC β-1 and homologous sites are found in the PKC β-1 sequence. It should be noted that while all putative autophosphorylation sites are still present in both mutants, enzymatic activity is lost in the mutant CD15 but little affected in ND12.

Expressed PKC alpha responds to a broad spectrum of tumor promoter agonists and antagonists and PKC activators and inhibitors.

We have demonstrated that mammalian PKC activity expressed in yeast is modulated by the same classes of PKC activators and inhibitors in vitro and in vivo as in mammalian cells. PKC activators PMA, PDBu, 12- deoxyphorbol 1 3-phenylacetate (dPP), as well as ingenol 3,20-dibenzoate (ID), 6-(N-decylamino)-4-hydroxymethylindole (DHI), 3-(N-acetylamino)-5(N-decyl-N-methylamino) benzyl alcohol (ADMB), (−)-indolactam V, and mezerein all efficiently activated PKC alpha in vitro. The second cys-repeat in C1 appears to be important in the indolactam V interaction with PKC. Our data suggest that both cys-repeats or even the complete C1 region are required for indolactam V activation of PKC while only the first cys-repeat is critical in the mezerein response. In contrast either cys-repeat of C1 is sufficient for the response and suggests a comparable mechanism of action for PMA and dPP. PKC alpha catalytic activity is efficiently inhibited by H-7, psychosine, trifluoperazine, polymyxin B, staurosporine, acridine orange, dequalinium and chelerythrine. The interaction with acridine orange and polymyxin B appears to involve the first cys-repeat of C1 which may consequently play a role in the phospholipid binding site, the proposed target site of polymyxin B and trifluoperazine. The interaction with trifluoperazine appears to depend on an intact C2 region which may suggest a fole of this region in phospholipid binding as well. Specific sequences in the C2 region have been identified which may be a critical target in the interaction with the anti-cancer drug dequalinium.

Phenotypic screen for tumor promoter agonist or antagonist or PKC inhibitor or activator activity.

Our findings indicate that normal and mutant forms of mammalian PKC are functionally expressed in yeast and display distinct phorbol ester-responsive, constitutive or lack of catalytic and biological response are specific for wild type and different classes of mutations. These distinct levels of PKC activity cause a proportional increase in the cell doubling time which results in a proportional decrease in yeast colony size on agar plates. Even small differences in PKC activity are translated into visible differences in colony size, which permits the screening of compounds as tumor promoter agonists or antagonists or as PKC inhibitors or activators.

Compounds can be tested for tumor promoter agonist or antagonist activity or for PKC inhibitor or activator activity by adding them to growth medium containing mammalian PKC expressing-yeast, incubating the treated cells and determining the effect of the treatment on the growth rate of the cells. The growth rate of the treated cells can be compared to an appropriate control, e.g., untreated PKC-expressing yeast cells. More than one compound can be added to the yeast to investigate the joint action of more than one compound on the growth rate. For example, a candidate compound can be evaluated for its tumor promoter antagonist activity by administering the compound and a known tumor promoter to the cells. A decrease in the effect of the tumor promoter is indicative of the tumor promoter antagonist activity of the compound.

The tests can be performed on small tubes or in multi-well plates and can be adopted for automated analysis by methods known to those skilled in the art.

Since yeast growth can be easily monitored in a small test tube or on multi-well plates and a result is usually obtained within hours to days, this screen is suitable for large scale product screening. It can be applied to test the potential of any cosmetic or pharmaceutical product as tumor promoter agonists or antagonists. Large numbers of products can be rapidly screened for their cancer hazard potential. At the same time the screen will allow a basic evaluation of the general PKC-non-specific cytoxicity of the tested product towards control yeast cells.

A rapid approach for PKC structure-function analysis.

The yeast cell/mammalian PKC system can also be used for the phenotypic classification of PKC mutants with altered basal or ligand-activated characteristics out of a large background of inactive PKC forms Basal and phorbol ester-stimulated states of normal PKC alpha and mutant D172-225 define four levels of catalytic activity which result in proportional differences in yeast colony size and demonstrate the resolution and sensitivity of the screen. Our approach allows the evaluation of hundreds of individual colonies on a single culture plate which permits the routine screening of thousands of individual mutations in one experiment. The experimental background created by normal variation in yeast colony size can be reduced by replica-plating and successive screening steps including liquid culture of promising mutant candidates which allows most sensitive quantification of PKC activity. The screen is particularly suitable for random mutagenesis strategies which introduce major structural changes and result in large numbers of inactive PKC forms. Rare mutations with varying levels of PKC activity can be identified and quantified in this way. This strategy provides significant advantages over site-directed mutagenesis approaches since large numbers of structural changes can be rapidly tested and changes are not limited to the structural predictions of the investigator.

Other embodiments are within the following claims:

---

I claim:

1. A method of screening a compound for the ability to modulate a PKC-mediated growth response comprising, supplying a yeast cell transformed to express a mammalian PKC, contacting said yeast cell with a compound to be screened, wherein said compound binds to said mammalian PKC; and determining the rate of growth of said yeast cell, an effect on said rate of growth being indicative of the ability of said compound to modulate said PKC-mediated growth response.

2. The method of claim 1, wherein said cell is a Saccharomyces cell.

3. The method of claim 2, wherein said cell is a *Saccharomyces cerevisiae* cell.

4. The method of claim 1, wherein said PKC is a conventional PKC.

5. The method of claim 4, wherein said PKC is selected from the group consisting of PKC alpha, PKC beta-1, PKC beta-2, and PKC gamma.

6. The method of claim 1, wherein said PKC is a PKC which lacks a C2 region.

7. The method of claim 5, wherein said PKC is PKC alpha.

8. The method of claim 5, wherein said PKC is PKC beta-1.

9. The method of claim 5, wherein said PKC is PKC beta-2.

10. The method of claim 5, wherein said PKC is PKC gamma.

11. The method of claim 6, wherein said PKC is selected from the group consisting of PKC delta, PKC epsilon, PKC zeta, and PKC eta.

12. The method of claim 11, wherein said PKC is PKC delta.

13. The method of claim 11, wherein said PKC is PKC epsilon.

14. The method of claim 11, wherein said PKC is PKC zeta.

15. The method of claim 11, wherein said PKC is PKC eta.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

AGCTTAAAAA A  11

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

ATTTTTTGTA C   11

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TAACTAACTA AT   12

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

ATTGATTGAT TAGATC   16

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TCGACAAAAA AAAAAATGGC T   21

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GTTTTTTTTT TTACCGA   17

(2) INFORMATION FOR SEQ ID NO:7:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

Arg Phe Ala Arg Lys Gly Ser Leu Arg Gln Lys Asn Val
1               5                   10